(12) United States Patent
Castro-Benitez et al.

(10) Patent No.: US 10,761,016 B2
(45) Date of Patent: Sep. 1, 2020

(54) QUANTIFICATION DEVICE FOR LIPID AND/OR PROTEIN LEVELS IN HEPATIC TISSUE

(71) Applicant: Institut Georges Lopez, Lissieu (FR)

(72) Inventors: Carlos Castro-Benitez, Paris (FR); George Antoine Lopez, Anse (FR)

(73) Assignee: Institut Georges Lopez (FR)

( * ) Notice: Subject to any disclaimer, the term of this patent is extended or adjusted under 35 U.S.C. 154(b) by 0 days.

(21) Appl. No.: 16/289,839

(22) Filed: Mar. 1, 2019

(65) Prior Publication Data

US 2019/0277752 A1    Sep. 12, 2019

(30) Foreign Application Priority Data

Mar. 9, 2018   (FR) ..................... 18 52044

(51) Int. Cl.
| | |
|---|---|
| *G01J 5/02* | (2006.01) |
| *G01N 21/35* | (2014.01) |
| *A61B 5/00* | (2006.01) |
| *G01J 3/10* | (2006.01) |
| *G01J 3/42* | (2006.01) |

(Continued)

(52) U.S. Cl.
CPC ........... *G01N 21/35* (2013.01); *A61B 5/0075* (2013.01); *A61B 5/0086* (2013.01); *A61B 5/416* (2013.01); *A61B 5/4244* (2013.01); *A61B 5/4872* (2013.01); *G01J 3/10* (2013.01); *G01J 3/42* (2013.01); *A61B 2505/05* (2013.01);

(Continued)

(58) Field of Classification Search
CPC ............ G01N 21/35; G01N 2201/068; G01N 2201/061; A61B 5/0086; A61B 5/4872; A61B 5/0075; A61B 5/4244; A61B 5/416; A61B 2505/05; G01J 3/42; G01J 3/10; G01J 3/12; G01J 3/0205
See application file for complete search history.

(56) References Cited

U.S. PATENT DOCUMENTS

| | | | |
|---|---|---|---|
| 8,209,128 B1* | 6/2012 | Gourley .............. | G01N 33/574 356/318 |
| 9,939,370 B2* | 4/2018 | Diem .................... | G01N 21/31 |

(Continued)

OTHER PUBLICATIONS

Diem et al., "Infrared spectroscopy of human cells and tissue. VII. Strategies for analysis of infrared tissue mapping data and applications to liver tissue," 2000, Biopolymers, vol. 57, pp. 282-290. (Year: 2000).*

(Continued)

*Primary Examiner* — Kiho Kim
(74) *Attorney, Agent, or Firm* — Forge IP, PLLC

(57) ABSTRACT

A quantification device for the level of lipids and/or proteins present within hepatic tissues. The Device includes: a light source, having at least one vacuum tungsten lamp with a total power of between 0.5 and 2 watts, with a total brightness of between 1000 and 2000 lumens and a total color temperature of between 6000 and 10000 degrees Kelvin; a photosensitive sensor having a sensitivity wavelength of between 800 nm and 2450 nm, configured to capture the light emitted from the light source after diffraction within liver tissues; means for extracting a diffraction spectrum of the light according to an image captured by the photosensitive sensor; and means for analyzing the spectrum in order to determine a level of lipids and/or proteins.

11 Claims, 2 Drawing Sheets

(51) Int. Cl.
  *G01J 3/02* (2006.01)
  *G01J 3/12* (2006.01)
(52) U.S. Cl.
  CPC ............... *G01J 3/0205* (2013.01); *G01J 3/12* (2013.01); *G01N 2201/061* (2013.01); *G01N 2201/068* (2013.01)

(56) References Cited

U.S. PATENT DOCUMENTS

| | | | |
|---|---|---|---|
| 2008/0306337 | A1 | 12/2008 | Livingston et al. |
| 2014/0131578 | A1 | 5/2014 | Hruska et al. |
| 2014/0330106 | A1* | 11/2014 | Banerjee ................ A61B 5/004 600/410 |
| 2016/0327524 | A1* | 11/2016 | Wang .................. G01N 29/0654 |
| 2017/0138860 | A1* | 5/2017 | Huang .................. A61B 5/0075 |
| 2018/0146857 | A1* | 5/2018 | Gonzalez Fernandez ................... A61B 5/00 |
| 2018/0214025 | A1* | 8/2018 | Homyk ................ A61B 5/0082 |

OTHER PUBLICATIONS

Le Naour F, Bralet M-P, Debois D, Sandt C, Guettier C, et al. (2009) "Chemical Imaging on Liver Steatosis Using Synchrotron Infrared and ToF-SIMS Microspectroscopies". PLoS One 4(10): e7408. doi:10.1371/journal.pone.0007408.

Le Naour, F, et al. (2012) "In Situ Chemical Composition Analysis of Cirrhosis by Combining Synchrotron Fourier Transform Infrared and Synchrotron X-ray Fluorescence Microspectroscopies on the Same Tissue Section". dx.doi.org/10.1021/ac302072t Anal. Chem. 2012, 84, 10260-10266.

Peng, C, et al. (2016), "Discrimination of cirrhotic nodules, dysplastic lesions and hepatocellular carcinoma by their vibrational signature". Journal of Translation Medicine (2016) 14:9. DOI 10.1186/s12967-016-0763-6.

* cited by examiner

QUANTIFICATION DEVICE FOR LIPID AND/OR PROTEIN LEVELS IN HEPATIC TISSUE

TECHNICAL FIELD

The invention relates to a quantification device for the level of lipids and/or proteins within hepatic tissue.

More particularly, the invention relates to a device for estimating the level of steatosis within the liver. The invention finds a particularly advantageous application in improving liver transplant conditions.

PRIOR ART

The first step within the context of liver transplantation consists in determining whether the graft, that is to say the organ and the adjacent anatomical structures thereof, are healthy. The first assessment is generally performed prior to the transplantation in examining the medical records of the donor. The medical records are however often insufficient for allowing the surgeon to estimate the quality of the graft.

Upon removal by extraction of the liver from the donor, the surgeon performs a second visual assessment by means of palpation and an evaluation of the consistency, color and size of the graft. In France, about 100 grafts a year are not removed, insofar as the surgeon determines that the liver is non-conformant due, in particular, to the steatotic appearance thereof.

Once the graft is removed, it is transported to the center where the recipient is waiting for a transplant. The graft is subsequently examined again, visually by the surgeon who will performs the transplant. The surgeon palpates the graft and looks at the color and consistency of it. In France, this latter examination leads to the rejection 30 of about 30 grafts a year because the surgeon in charge of transplantation judges that the appearance of the liver is non-conformant, particularly due to steatosis.

Hepatic steatosis is a liver pathology associated with an excess of lipids, mainly triglycerides, within the cytoplasm of hepatocytes. The prevalence of this disease is 20% to 30% in developed countries. This is therefore a common disease, whose prevalence tends to increase with the increase in cases of obesity and diabetes.

Two types of hepatic steatosis are observed, micro-vesicular steatosis with varied etiology, which is characterized by the presence of multiple small lipid vacuoles within the cytoplasm and wherein the presence thereof does not lead to displacement of the nucleus of hepatocytes. The second type of steatosis, the most severe, is macrovacuolar steatosis, wherein one of the etiologies is the excessive consumption of alcohol. This type of steatosis is characterized by a single large lipid vacuole that displaces the nucleus of hepatocytes.

Although surgeons are experienced in these kinds of observations, this visual assessment and palpation is often difficult to achieve due in particular to the presence of blood around the liver during removal. Furthermore, this assessment is subjective, explaining why results may differ from one surgeon to another.

Steatosis may be characterized by the presence of an accumulation of proteins within the cytoplasm of hepatocytes. For example, liver cells may contain an excess of enzymes such as transaminases (alanine aminotransferase/ ALAT or aspartate aminotransferase/ASAT) or gamma-glutamyl transpeptidase (Gamma-GT). Within the context of steatosis, the hepatocytes can also be characterized by the presence of Mallory bodies, that is to say, osinophilic intrahepatocytic aggregates of intermediate prekeratin microfilaments from the cytoskeleton of the hepatocyte.

Thus, a more efficient method to estimate the level of steatosis of a graft has been studied.

Recent studies have shown that it is possible to quantify the presence of steatosis in a graft by the diffraction of infrared light within the graft: "Chemical Imaging on Liver Steatosis Using Synchrotron Infrared and ToF-SIMS Microspectroscopies", Le Naour &all, PLoS ONE, October 2009, volume 4, issue 10, e7408, "In Situ Chemical Composition Analysis of Cirrholis by Combining Synchrotron Fourier Transform Infrared and Synchrotron X-ray Fluorescence Microscopies on the Same Tissue Section", Le Naour & all, analytical chemistry, 2012, 84, 10260-10266, and, "Discrimination of cirrhotic nodules, dysplastic lesions and hepatocellular carcinoma by their vibrational signature", Peng & all, J. Transl. Med., 2016, 14:19. The results of this work are also mentioned within document US 2008/306337.

To conduct these studies, a biopsy of the graft is performed at the moment of removing the graft. The sample thus collected is transported to a research laboratory that analyzes the diffraction of infrared light within the biopsy.

This analysis is particularly complex. Indeed, in order to obtain the required infrared light, these studies describe the use of the "SOLEIL" synchrotron allowing for a light source of high brightness in the spectral region 1-100 microns with detection optimization in the region of 2.5-100 microns. This specific source is coupled to an FTIR infrared microscope.

These laboratory studies can accurately detect the level of steatosis of a sample and thereby determine whether the sample, and by generalization the entire liver, is healthy.

Advantageously, if the liver contains less than 5% lipids, this organ is considered to be healthy.

The level of steatosis may however vary from one region to another of the same liver. Thus, measurements from a liver biopsy cannot be generalized for the entire organ and does not make it possible to quantify the state of health thereof.

In addition, the use of an FTIR infrared microscope for performing such measurements requires the use of a specifically equipped laboratory, often remote from graft removal and transplantation areas.

Finally, given the fragility of the graft, it is necessary to minimize the delay between the removal and transplantation of the graft. Under these conditions, the time required to transport a sample of a graft to a specifically equipped analysis laboratory may limit the possibility of transplanting the graft.

Optimizing the hepatic tissue analysis conditions would shorten this delay.

The document US 2014/131578 describes a portable spectrometer incorporating a vacuum tungsten lamp. This spectrometer is described more particularly for use in the pharmaceutical industry, in particular for analyzing raw materials.

In view of the specificity of those light sources that can be used with grafts such as those described in the scientific studies mentioned above, the spectrometer illustrated in US 2014/131578 would appear to be inappropriate for quantifying the level of lipids and/or proteins present within hepatic tissues.

The technical problem of the invention therefore consists in improving the existing hepatic tissue analysis process by diffraction.

DISCLOSURE OF THE INVENTION

The Applicant has found that the diffraction of broad-spectrum light makes it possible to obtain diffractions that reveal the level of lipids and/or proteins present within hepatic tissues. In so doing, the invention eliminates the use of very specific spectrum infrared light and makes it possible to implement a much simpler and much smaller analysis device. It follows that the analysis device may be arranged within the operating room in such a way that an assessment of a graft may be carried out by broad-spectrum light diffraction within the graft before the extraction of the graft, and without performing a biopsy on the organ. In addition, several analyses can be performed on multiple parts of the graft without leading to graft lesions, that is to say without performing a biopsy.

For this purpose, in a first aspect, the invention relates to a quantification device for the level of lipids and/or proteins present within hepatic tissues, said device comprising:
- a light source configured in order to project said light upon hepatic tissues to be analyzed;
- a photosensitive sensor configured in order to capture said light emitted from said light source after diffraction within said hepatic tissues;
- means for extracting a diffraction spectrum of said light according to an image captured by said photosensitive sensor; and
- means for analyzing said spectrum in order to determine a level of lipids and/or proteins present within said hepatic tissues.

The invention is characterized in that:
- said light source is in the form of at least one vacuum tungsten lamp with a total power of between 0.5 and 2 watts, with a total brightness of between 1000 and 2000 lumens and a total color temperature of between 6000 and 10000 degrees Kelvin; and
- said photosensitive sensor has a sensitivity wavelength of between 800 nm and 2450 nm.

According to an embodiment of the invention, said photosensitive sensor has a sensitivity wavelength of between 1100 nm and 2450 nm.

Against all expectations, the use of a vacuum tungsten lamp of a suitable power is sufficient to replace the infrared source of a synchrotron insofar as the diffractions revealed by the photosensitive sensor makes it possible to estimate the level of lipids and/or proteins present within hepatic tissues.

The size of a vacuum tungsten lamp being much smaller than the size of the light sources of the prior art, with a ratio of at least 100, it is possible to achieve a completely different implementation of the state of the art. In particular, it is no longer necessary to use a laboratory with specific equipment dedicated to performing the analysis. For example, the light source and the sensor can be implemented on an electronic device the size of a smart phone.

According to one embodiment, the device comprises two vacuum tungsten lamps. This embodiment facilitates the implementation of the light source in such a way as to obtain the required total characteristics of the light source.

According to one embodiment, said light source and said photosensitive sensor are arranged at a maximum distance of 3 cm from each other. Thus, the light source is very close to the photosensitive sensor and the light is captured by reflection of the light upon the hepatic tissues.

This solution is particularly advantageous compared to the state of the art that uses a light source arranged above a sample and a sensor arranged below the sample. Indeed, this solution makes it possible to use a single control unit for performing the emission and reception of the light.

According to one embodiment, said light source is powered using a voltage of between 3 and 15 Volts. This embodiment make it possible to supply the light source with a small amount of energy and, thus, to facilitate the integration of the light source power supply.

According to one embodiment, said light source is powered using a current of between 0.1 and 0.4 Amperes. This embodiment make it possible to supply the 30 light source with a small amount of energy and, thus, to facilitate the integration of the light source power supply.

According to one embodiment, said photosensitive sensor corresponds to an InGas type detector. This embodiment makes it possible to effectively detect the diffracted light whilst allowing for the integration of the photosensitive sensor within a portable device.

According to a second aspect, the invention relates to a method for quantifying the level of lipids and/or proteins present within hepatic tissues from a donor by means of an analysis device according to the first aspect of the invention, said method comprising the steps of:
- positioning said light source close to the hepatic tissues to be analyzed;
- emitting light onto the hepatic tissues to be analyzed;
- receiving the light emitted by said light source and diffracted within said hepatic tissues by the photosensitive sensor;
- extracting a diffraction spectrum of said light according to an image captured by said photosensitive sensor; and
- analyzing said spectrum in order to determine the level of lipids and/or proteins present within said hepatic tissues.

According to one embodiment, the positioning step is performed prior to the extraction from the donor, that is to say when the liver to be transplanted is present within the body of the donor.

According to one embodiment, the analysis step is performed using reference images of hepatic tissues for distinct levels of lipids and/or proteins.

According to one embodiment, said method comprises a removal, or non-removal, decision-making step as a function of the level of lipids and/or proteins present within said analyzed hepatic tissues.

BRIEF DESCRIPTION OF THE FIGURES

The method for implementing the invention and its advantages will become more apparent from the following disclosure of the embodiment, given by way of a non-limiting example, supported by the attached figures wherein

FIG. 1: a schematic representation of a quantification device for levels of lipids and/or proteins when used in an operating theater according to one embodiment of the invention; and FIG. 2: a flowchart of a method for the quantification of the level of lipids and/or proteins by means of the device of FIG. 1.

DETAILED DESCRIPTION OF THE INVENTION

Figure 1:
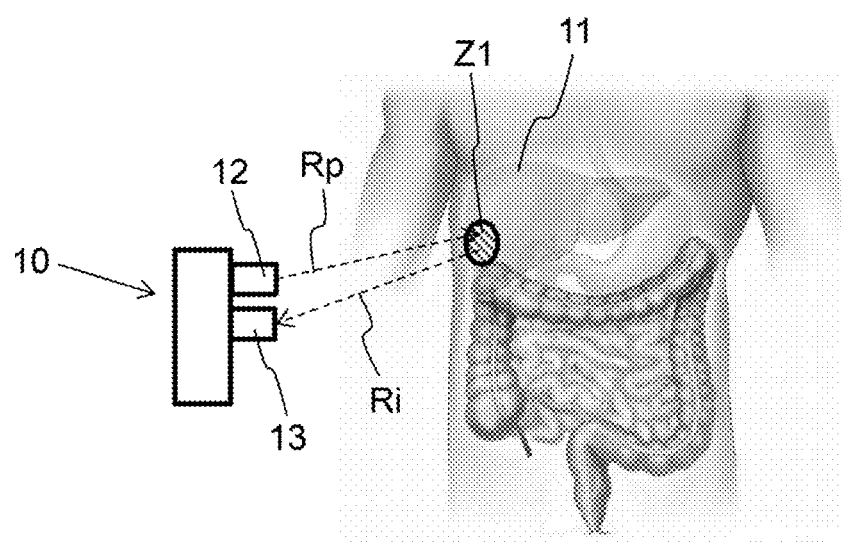
FIGS. 1 and 2 represent.

FIG. 1 shows a donor arranged on an operating table during a liver removal operation. Preferably, the body of the donor is open such that the liver is visible and accessible.

Figure 2:
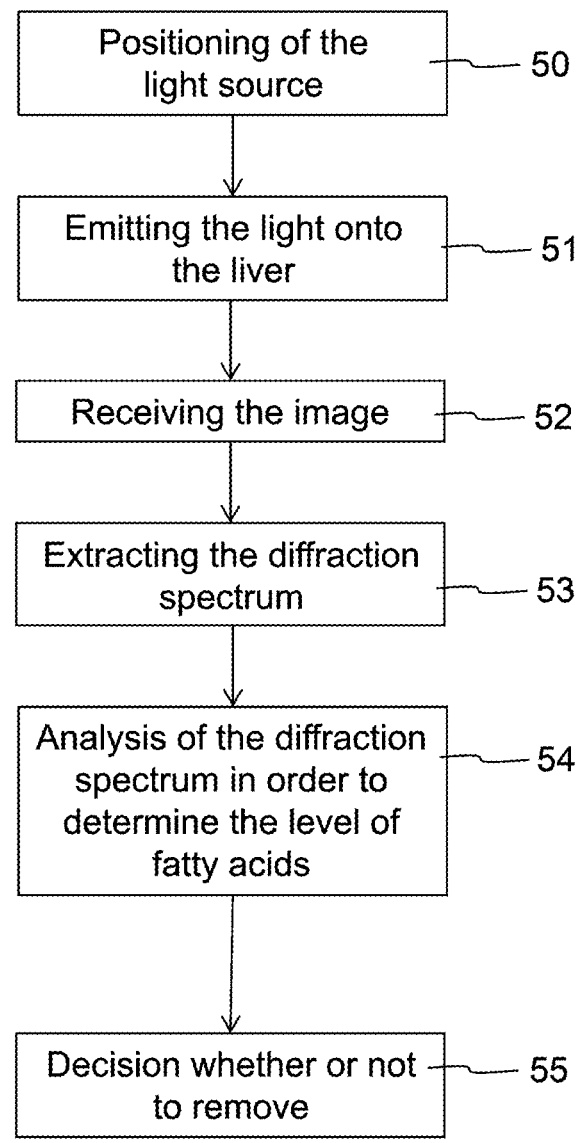

In a first step 50, shown in FIG. 2, a device 10 according to the invention is arranged facing the liver of the donor, for example at a distance of between 10 and 20 cm from the liver of the donor. The user of the device 10, for example an operating theater surgeon or nurse (IBODE), may then control the initiation of a level of lipids and/or proteins measurement.

This operation can be performed by pressing a push button, not shown, arranged on the device 10.

In a second step 51, the device 10 proceeds with the emission of a broad spectrum light Rp by means of a light source 12 arranged opposite the liver. Said light source 12 is in the form of at least one vacuum tungsten lamp with a total power of between 0.5 and 2 watts, with a total brightness of between 1000 and 2000 lumens and a total color temperature of between 6000 and 10000 degrees Kelvin.

Preferably, the light source 12 is implemented by means of two broad spectrum vacuum tungsten lamps.

For example, each vacuum lamp has a power of 0.6 watts in order to obtain the total power within the required range. Alternatively, the number of tungsten vacuum lamps may be higher, for example three or four lamps can be used without changing the invention. The greater the number of lamps, the easier the lamps are to implement insofar as they should be of lower performance. However, the number of lamps increases the size of the device 10.

In order to limit the size of the device 10, lamps are preferably sought that have limited power consumption, typically between 3 and 15 volts and 0.4 and 0.1 amperes. In doing so, it is possible to use a power supply with a small size in order to supply power to the lights. For example, two vacuum lamps can be used with a power of 0.6 watts and a power supply of 5 volts and 0.12 amperes.

When the light source 12 emits the broad-spectrum light Rp, this light covers an area Z1 of the liver. In coming into contact with said area Z1, the light Rp is diffracted in all directions thereby forming an incident ray Ri in the direction of the device 10.

Said incident ray Ri is captured by a photosensitive sensor 13 arranged adjacent to the light source 12, for example at a maximum distance of 5 cm.

In the example of FIG. 1, the light source 12 and the photosensitive sensor 13 are mounted on the same housing. Alternatively, these optical elements can be mounted on two separate housings without changing the invention.

Furthermore, these optical elements may also be mounted on a smart phone configured in such a way as to perform the processing of the received signal Ri or in order to transmit the received signal to a processing system.

The photosensitive sensor 13 has a sensitivity wavelength of between 800 nm and 2450 nm, and in one embodiment of the invention, between 1100 and 2450 nm. Thus, although the light Rp emitted by the light source 12 is broad-spectrum, the photosensitive sensor 13 captures at least those wavelengths received within the range between 800 nm and 2450 nm or the range between 1100 and 2450 nm, or only part of the light spectrum Rp. For example, the photosensitive sensor 13 may correspond to an InGas type detector.

In a step 52, this photosensitive sensor 13 acquires a spectral image of the variations in the diffracted light Ri over the area Z1 of the liver. Processing of the image is then implemented in order to define the quality of the liver.

In a first step 53 for processing the image from the photosensitive sensor 13, the spectrum of the diffracted light Ri is sought. This spectrum is compared, in a step 54, with pre-recorded spectra for various liver conditions. For example, this comparison can be performed by a neural network configured in such a way as to search for maximum correlation between the spectrum resulting from step 53 and the pre-recorded spectra associated with various liver conditions. Conventionally, this neural network is expected to undergo a learning stage wherein typical spectra are recorded for various liver conditions. For example, ten spectra can be recorded for a liver with a 10% level of lipids and/or proteins, ten spectra for a liver with a 20% level of lipids and/or proteins, and so on up to to 90% of lipids and/or proteins.

Thus, the neural network compares the spectrum resulting from step 53 with a large quantity of pre-recorded spectra and searches for maximum correlation.

This correlation search step can, for example, be achieved by means of an RBF type neural network, or "Radial Basic Function" in English literature. This RBF neural network has a set of hidden neurons associated with each pre-recorded spectrum. Each hidden neuron performs a calculation for the correlation between the spectrum resulting from step 53 and a pre-recorded spectrum.

Each hidden neuron produces a score for the correlation between the spectrum resulting from step 53 and a pre-recorded spectrum. This correlation score indicates the similarity between the spectrum resulting from step 53 and the pre-recorded spectrum. An output neuron determines the maximum correlation scores in order to determine which prerecorded spectrum corresponds to the spectrum resulting from step 53. This output neuron is preferably associated with a threshold correlation score, below which the neural network considers that an acceptable correlation has not been found.

Alternatively, other architectures and spectrum analysis strategies can be used without changing the invention.

When the spectrum is correlated with a previously recorded spectrum, the level of lipids and/or proteins associated with the pre-recorded spectrum is searched for, for example the pre-recorded spectrum could have been recorded with a 20% level of lipids and/or proteins. This lipids and/or proteins measurement can be implemented using known means for estimating levels of lipids and/or proteins, for example using the means described within the publications: "Chemical Imaging on Liver Steatosis Using Synchrotron Infrared and ToF-SIMS Microspectroscopies", Le Naour &all, PLoS ONE, October 2009, volume 4, issue 10, e7408, "In Situ Chemical Composition Analysis of Cirrholis by Combining Synchrotron Fourier Transform Infrared and Synchrotron X-ray Fluorescence Microscopies on the Same Tissue Section", Le Naour & all, analytical chemistry, 2012, 84, 10260-10266, and, "Discrimination of cirrhotic nodules, dysplastic lesions and hepatocellular carcinoma by their vibrational signature", Peng & all, J. Transl. Med., 2016, 14:19.

Thus, the level of lipids and/or proteins of the measured spectrum is determined as a function of the level of lipids and/or proteins of the spectrum nearest that of the measured spectrum.

This estimate of the level of lipids and/or proteins is then transmitted to the user in a step 55. This transmission can be achieved by means of an LCD arranged on the device 10 or directly on the smart phone of the user by means of an application connected to the device 10.

Finally, the surgeon may use this information concerning the level of lipids and/or proteins in order to estimate with greater precision and speed whether or not the liver should be removed from the donor.

In conclusion, the invention improves the process of estimating the quality of the liver from a donor. Furthermore, this estimate can be performed directly within the body of the donor without performing a biopsy and an analysis with a microscope.

The invention claimed is:

1. Quantification device for the level of lipids and/or proteins present within hepatic tissues, said device comprising:
   a light source configured to project said light upon hepatic tissues to be analyzed;
   a photosensitive sensor configured to capture said light emitted from said light source after diffraction within said hepatic tissues;
   a processing system configured to;
   extract a diffraction spectrum of said light as a function of an image captured by said photosensitive sensor; and
   analyze said spectrum to determine a level of lipids and/or proteins present within said hepatic tissues;
   wherein:
   said light source is in the form of at least one vacuum tungsten lamp with a total power of between 0.5 and 2 watts, with a total brightness of between 1000 and 2000 lumens and a total color temperature of between 6000 and 10000 degrees Kelvin; and
   said photosensitive sensor has a sensitivity wavelength of between 800 nm and 2450 nm.

2. Quantification device according to claim 1, wherein said photosensitive sensor has a sensitivity wavelength of between 1100 nm and 2450 nm.

3. Quantification device according to claim 1, wherein the device comprises two vacuum tungsten lamps.

4. Quantification device according to claim 1, wherein said light source and said photosensitive sensor are arranged at a maximum distance of 3 cm from each other.

5. Quantification device according to claim 1, wherein said light source is supplied with a voltage of between 3 and 15 Volts.

6. Quantification device according to claim 1, wherein said light source is supplied with a current of between 0.1 and 0.4 Amperes.

7. Quantification device according to claim 1, wherein said photosensitive sensor corresponds to an InGas type detector.

8. A method for quantifying the level of fatty acids and/or proteins present within hepatic tissues from a donor by means of an analysis device according to claim 1, wherein said method comprises the following steps:
   positioning said light source close to the hepatic tissues to be analyzed;
   emitting light onto the hepatic tissues to be analyzed;
   receiving the light emitted by said light source and diffracted within said hepatic tissues by means of a photosensitive sensor;
   extracting a diffraction spectrum of said light according as a function of an image captured by said photosensitive sensor; and
   analyzing said spectrum to determine the level of lipids and/or proteins present within said hepatic tissues.

9. Method according to claim 8, wherein the positioning step is performed whilst the hepatic tissue is present in the body of the donor, advantageously before any transplantation step.

10. Method according to claim 8, wherein the analyzing step is performed using reference images of hepatic tissues for distinct levels of lipids and/or proteins.

11. Method according to claim 8, wherein said method comprises a removal, or non-removal, decision-making step as a function of the level of lipids and/or proteins present within said analyzed hepatic tissues.

* * * * *